United States Patent [19]

Bushnell

[11] Patent Number: 5,026,727

[45] Date of Patent: Jun. 25, 1991

[54] INSECTICIDAL COMPOUNDS

[75] Inventor: Michael J. Bushnell, Wokingham, England

[73] Assignee: Imperial Chemical Industries PLC, London, England

[21] Appl. No.: 413,560

[22] Filed: Sep. 28, 1989

[30] Foreign Application Priority Data

Sep. 28, 1988 [GB] United Kingdom ................ 8822793

[51] Int. Cl.⁵ .................. C07C 43/225; C07C 255/03; A01N 37/34; A01N 31/14

[52] U.S. Cl. ..................................... 514/520; 514/721; 568/637; 568/641; 558/389

[58] Field of Search ............... 568/645, 646, 637, 641; 514/721, 520; 558/389

[56] References Cited

U.S. PATENT DOCUMENTS 4,678,811  7/1987  Franke et al. ........................ 514/721

Primary Examiner—Alan L. Rotman
Attorney, Agent, or Firm—Cushman, Darby & Cushman

[57] ABSTRACT

Insecticidal and acaricidal compounds of formula:

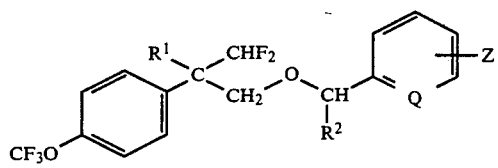

and stereoisomers thereof, where $R^1$ represents $C_{1-4}$ alkyl, $R^2$ represents H, CN, $CH_3$, C≡CH or $CF_3$; Q represents CH or N; and Z represents one or more substituents selected from fluoro, benzyl, phenoxy and halophenoxy.

5 Claims, No Drawings

INSECTICIDAL COMPOUNDS

This invention relates to novel fluorinated ethers useful as insecticides and acaricides, to compositions comprising them and to methods of combating insect and acarine pests therewith.

European Patent Application No. 179,018-A describes insecticidal and acaricidal, fluorinated ethers having the general formula:

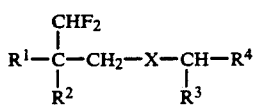

in which $R^2$ is hydrogen or alkyl, $R^3$ is hydrogen, cyano or ethynyl, $R^4$ is a substituted or unsubstituted phenyl or pyridyl group, and $R^1$ is a substituted or unsubstituted aryl group. EP 179,018 discloses generically compounds in which $R^1$ is a haloalkoxy phenyl group, and specifically discloses examples in which $R^1$ is a 4-difluoromethoxyphenyl or a 4-(2-fluoroethoxy)phenyl group.

We have now found that certain novel compounds falling within the disclosure of EP 179,018, for which the group $R^1$ represents 4-(trifluoromethoxy)phenyl, possess unexpectedly superior insecticidal properties, and in particular exhibit substantially higher levels of acaricidal activity than the specifically disclosed haloalkoxyphenyl compounds of EP 179,018. Accordingly in a first aspect, the invention provides compounds of formula (I):

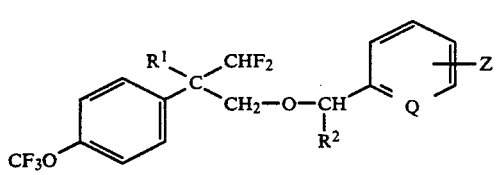

and stereoisomers thereof, wherein $R^1$ represents alkyl containing up to four carbon atoms; $R^2$ is selected from hydrogen, cyano, methyl, trifluoromethyl and ethynyl; Q is selected from carbon bearing a hydrogen atom and nitrogen, and Z represents one or more substituents selected from fluoro, benzyl, phenoxy, chlorophenoxy, fluorophenoxy and bromophenoxy. Preferred compounds according to the invention are those wherein $R^1$ represents methyl and wherein the group

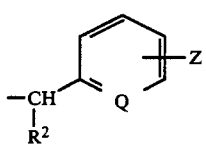

is selected from $E^1$ to $E^9$, where $E^1$ to $E^9$ have the meanings given below:

$E^1$: 3-phenoxybenzyl
$E^2$: 3-(4-chlorophenoxy)benzyl
$E^3$: 4-fluoro-3-phenoxybenzyl
$E^4$: 4-fluoro-3-(4-chlorophenoxy)benzyl
$E^5$: 3-benzyl-4-fluorobenzyl
$E^6$: (6-phenoxypyrid-2-yl)methyl
$E^7$: 1-cyano-1-(3-phenoxyphenyl)methyl
$E^8$: 1-(6-phenoxypyrid-2-yl)ethyl
$E^9$: 2,2,2-trifluoro-1-(6-phenoxypyrid-2-yl)ethyl.

Particular examples of compounds according to the invention include:

1,1-difluoro-2-methyl-2-(4-trifluoromethoxyphenyl)-3-(4-fluoro-3-phenoxybenzyloxy)propane, hereinafter referred to as Product I, and stereoisomers thereof, 1,1-difluoro-2-methyl-2-(4-trifluoromethoxyphenyl)-3-(3-phenoxybenzyloxy)propane, hereinafter referred to as Product II, and stereoisomers thereof, 1,1-difluoro-2-methyl-2-(4-trifluoromethoxyphenyl)-3-(3-benzyl-4-fluorobenzyloxy)propane, hereinafter referred to as Product III, and stereoisomers thereof, 1,1-difluoro-2-methyl-2-(4-trifluoromethoxyphenyl)-3-[3-(4-chlorophenoxy)benzyloxy]propane, hereinafter referred to as Product IV, and stereoisomers thereof.

The compounds according to formula (I) contain at least one asymmetrically substituted carbon, each of which may exist in one of two alternative configurations (the R-form and the S-form). The scope of this invention includes all single isomers and isomeric mixtures, including racemic mixtures, resulting from such asymmetric substitution within the compounds according to the invention.

The compounds of formula (I) and stereoisomers thereof may be prepared by reaction of an alcohol of formula (II):

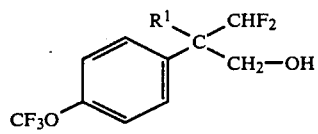

or a stereoisomer thereof, with a halide of formula (III):

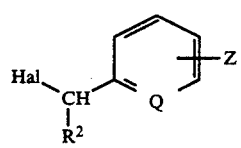

or a stereoisomer thereof, wherein $R^1$, $R^2$, Q and Z have any of the meanings given hereinabove and Hal represents halo, preferably bromo or chloro, the reaction preferably taking place in the presence of a base, optionally in a two phase system, catalysed by a phase transfer catalyst. The alcohols of formula (II) and stereoisomers thereof may be prepared by means of the processes described in Scheme I. Further details of these processes are given in the Examples hereinafter.

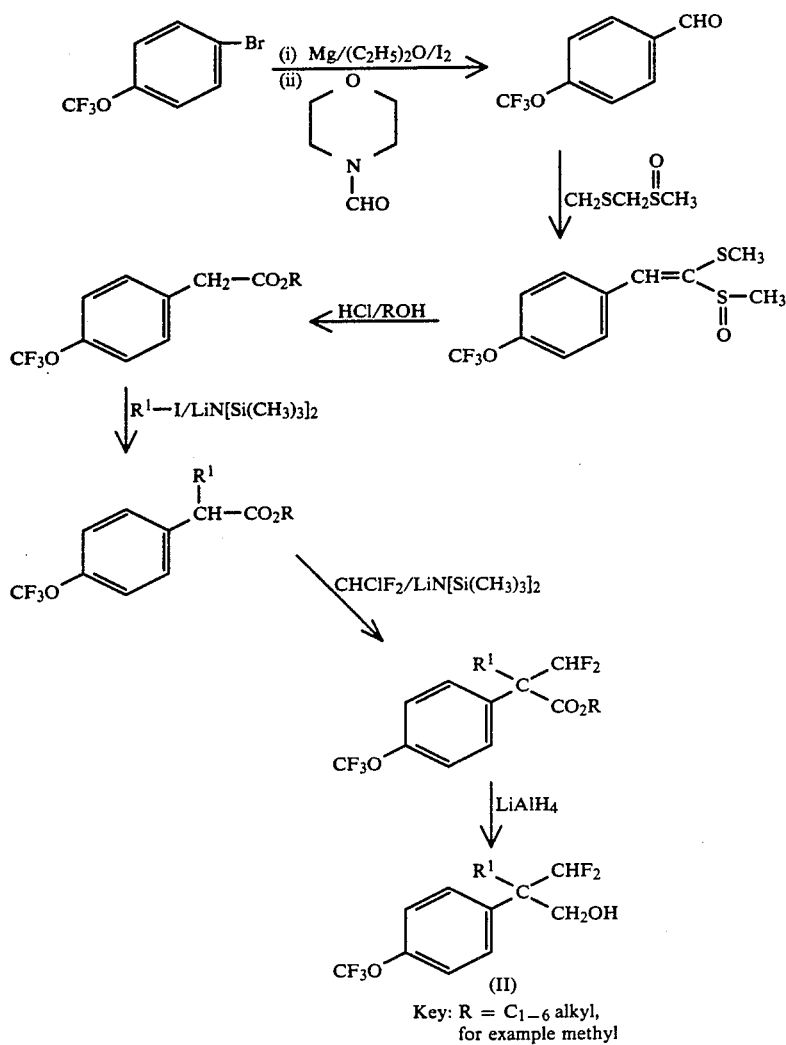

Scheme I

Key: R = $C_{1-6}$ alkyl,
for example methyl

Many of the intermediates described above are novel. In further aspects of the invention, therefore, there are provided:

a compound of formula:

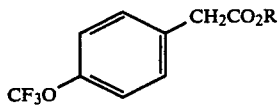

wherein R is alkyl containing up to six carbon atoms;

a compound of formula:

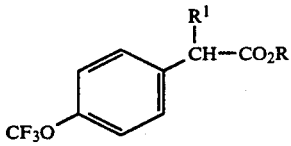

or a stereoisomer thereof, wherein $R^1$ is alkyl containing up to four carbon atoms and wherein $R^1$ is alkyl containing up to six carbon atoms;

a compound of formula:

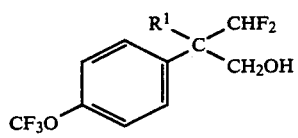

or a stereoisomer thereof, wherein $R^1$ is alkyl containing up to four carbon atoms and R is alkyl containing up to six carbon atoms; and a compound of formula:

or a stereoisomer thereof, wherein $R^1$ is alkyl containing up to four carbon atoms and R is alkyl containing up to six carbon atoms.

The compounds of formula I may be used to combat and control infestations of insect pests and also other invertebrate pests. They are particularly effective for the control of acarine pests. The insect and acarine pests which may be combated and controlled by the use of the invention compounds include those pests associated with agriculture (which term includes the growing of crops for food and fiber products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence at the locus of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, methyl parathion, azinphos-methyl, demeton-S-methyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim, pyrimiphos-methyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones such as juvenile hormone, juvabione, or ecdysones;

(h) Pheromones;

(i) Organochlorine compounds such as benzene hexachloride, DDT, chlordane, endosulphan or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentezine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as aerosols, dips or sprays. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by convention spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitos)
*Anopheles spp.* (mosquitos)
*Culex spp.* (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Aonidiella spp.* (scale insects)
*Trialeuroides spp.* (white flies)
*Blattella germanica* (cockroaches)
*Blatta orientalis* (cockroaches)
*Periplaneta americana* (cockroaches)
*Spodoptera littoralis* (cotton leaf worm)
*Heliothis virescens* (tobacco budworms)
*Chortiocetes terminifera* (locusts)
*Diabrotica spp.* (rootworms)
*Nilaparvata lugens* (plant hoppers)
*Agrotis spp.* (cutworms)
*Chilo partellus* (maize stem borers)
*Nephotettix cincticeps* (leaf hoppers)

The compounds according to formula (I) and compositions comprising them exhibit a particularly high level of acaricidal activity, and are particularly useful in the control of acarine pests such as *Panonychus* spp. (for example *Panonychus ulmi* and *Panonychus citri*) and *Tetranychus* spp. (for example *Tetranychus urticae* and *Tetranychus cinnabarinus*). They may also be useful in combating insect and acarine pests which infest domestic animals, such as *Lucilia sericata*, and ixodid ticks such as *Boophilus* spp., *Ixodes* spp., *Amblyomma* spp., *Rhipicephalus* spp. and *Dermocentor* spp. They are effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic reasonance spectroscopy and infra red spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak, CPSil 5CB column of 12.5 m length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz $^1$H NMR spectrometry were performed using Jeol FX 90 Q, Jeol PMX60 SI and Jeol GX400 spectrometers respectively.

$^{19}$F NMR spectrometry was performed on a Jeol FX90Q spectrometer at a frequency of 84.26 MHz. All NMR shift values ($\delta$) are quoted in ppm relative to a standard (TMS or CFCl$_3$).

Molecular Ion (M+) peaks were determined on one of three mass spectrometers : Jeol DX303, Kratos MS80 or Hewlett Packard HP 5992.

EXAMPLE 1

This Example illustrates the preparation of 4-trifluoromethoxybenzaldehyde.

4-Bromotrifluoromethoxybenzene (60 g) was added slowly to a stirred mixture of magnesium (6.0 g) and iodine (0.05 g) in diethyl ether (500 cm$^3$). A vigorous reaction was observed and the mixture spontaneously warmed to the reflux temperature. Stirring was continued for a further hour after completion of the addition. The mixture was cooled to 0° C. and N-formylmorpholine (28.6 g) was added dropwise. On completion of the addition, the mixture was allowed to warm to the ambient temperature, and was stirred for a further one hour. The mixture was then quenched with water containing dilute hydrochloric acid and the ether layer separated. The aqueous phase was extracted with more diethyl ether and the combined ethereal layers washed twice with water and dried over anhydrous magnesium sulphate. Distillation of the solvent gave an oil (46.5 g), shown by GLC to contain a major product (85%) and some unreacted starting material (2%). The crude oil was purified by distillation under reduced pressure to give the title compound (28.5 g) in 92% purity.

Boiling Point:88°-92° C./20 mmHg $^1$H NMR (CDCl$_3$):7.2-7.4 (2H,m); 7.85-8.25 (2H,m); 10.01 (1H,s)

IR (liquid film):1710 cm$^{-1}$

GLC retention time:1.88 minutes.

EXAMPLE 2

This Example illustrates the preparation of 1-(2-methylthio-2-methylsulphinylethenyl)-4-trifluoromethoxybenzene.

A mixture of 4-trifluoromethoxybenzaldehyde (28.5 g), methyl methylthiomethyl sulphoxide (18.6 g), Triton B (3 cm$^3$) and dry tetrahydrofuran (50 cm$^3$) was heated at the reflux temperature, the progress of the reaction being monitored by GLC analysis of withdrawn samples at regular intervals. After 10 hours, GLC analysis suggested that the reaction rate had slowed considerably and the reaction was therefore worked up. The mixture was allowed to cool, then poured into water and the products extracted into diethyl ether. The combined ethereal extracts were washed twice with water and dried over anhydrous magnesium sulphate. Evaporation of the solvent under reduced pressure gave an oil which was purified by chromatography on a silica gel support, eluting with hexane containing 50% by volume ethyl acetate. The first material to be eluted was shown to be unreacted aldehyde; the second material to be eluted was identified as the title product (20.6 g).

$^1$H NMR (CDCl$_3$):2.35 (3H,s); 2.80 (3H,s); ca 7.3 (2H,broad d); 7.60 (1H,s); ca 7.95 (2H,d)

GLC retention time:5.96 minutes.

EXAMPLE 3

This Example illustrates the preparation of methyl 4-trifluoromethoxyphenylacetate.

Gaseous hydrogen chloride was passed into a solution of 1-(2-methylthio-2-methylsulphinylethenyl)-4-trifluoro-methoxybenzene (20.0g) in methanol (100 cm$^3$) over a period of 30 minutes; the temperature of the mixture rose spontaneously to 50° C. The hydrogen chloride source was removed and the mixture was heated at 50° C. for one hour. The mixture was then poured into water and the products extracted into chloroform. The organic extracts were washed twice with water and dried over anhydrous magnesium sulphate. Evaporation of the solvent under reduced pressure gave a mobile liquid (16.0 g) which was purified by distillation under reduced pressure in a Kugelrohr apparatus, the title product (14.0 g) distilling at a temperature range of 130°-140° C. at 20 mmHg.

$^1$H NMR (CDCl$_3$):3.71 (2H,s); 3.77 (3H,s); 7.2-7.4 (4H,m)

$^{19}$F NMR (CDCl$_3$):−58.4 (CF$_3$0,s)

GLC retention time:1.49 minutes.

EXAMPLE 4

This Example illustrates the preparation of methyl (RS)-2-(4-trifluoromethoxyphenyl)propanoate. Lithium bis-(trimethylsilyl)amide (27 cm$^3$ of a 1.0M solution in hexane) was added to a stirred solution of methyl 4-trifluoromethoxyphenylacetate (6.5 g) in dry tetrahydrofuran (50 cm$^3$) at the ambient temperature (ca. 20° C.) under an atmosphere of nitrogen; a moderate exotherm was observed. The mixture was stirred for a further one hour and a solution of excess methyl iodide (15.7 g) in dry tetrahydrofuran (50 cm$^3$) was added dropwise. Stirring was continued for a further one hour and the mixture was then poured into water and the products extracted into chloroform. The combined organic extracts were washed twice with water, dried over anhydrous magnesium sulphate and the solvent evaporated under reduced pressure to leave a mobile liquid. Analysis by GLC showed a major product (93%) with traces of unreacted starting material and dimethylated material. The crude product was purified by distillation under reduced pressure in a Kugelrohr apparatus, the title compound (5.2 g) boiling in the range 140°-150° C. at 20 mmHg.

$^1$H NMR (CDCl$_3$):1.5 (3H,d); 3.68 (3H,s); 3.73 (1H,g); 7.2-7.4 (4H,m)

GLC retention time:1.62 minutes.

EXAMPLE 5

This Example illustrates the preparation of methyl (RS)-1,1-difluoro-2-methyl-2-(4-trifluoromethoxyphenyl)propanoate.

A stirred solution of methyl (RS)-2-(4-trifluoromethoxyphenyl)propanoate (5.2 g) in dry tetrahydrofuran (100 cm$^3$) was cooled to −40° C. and lithium bis-(trimethylsilyl)amide (52 cm$^3$ of a 1.0 M solution in hexane) was added dropwise under a nitrogen atmosphere, the temperature of the reaction mixture being maintained below −30° C. during the addition. Stirring was continued at −30° C. for a further 30 minutes and gaseous chlorodifluoromethane was then bubbled into the stirred mixture; the mixture warmed spontaneously to −20° C. Introduction of chlorodifluoromethane was continued for a further 20 minutes. The reaction mixture was allowed to warm to the ambient temperature and then quenched with dilute aqueous hydrochloric acid solution. The aqueous mixture was extracted with chloroform, the organic layers were washed twice with water, dried over anhydrous magnesium sulphate and the solvent evaporated under reduced pressure to leave a mobile liquid. The crude reaction product was purified by distillation under reduced pressure in a Kugelrohr apparatus, the title compound (4.0 g) distilling in the range 140°-160° C. at 20 mmHg. This material was further purified by high pressure liquid chromatography to give the title compound (3.2 g) in 98.5% purity.

$^1$H NMR (CDCl$_3$):1.74 (3H,t,J=ca 2Hz); 3.8 (3H,s); 6.36 (1H,t,J=ca 56Hz); 7.15-7.45 (4H,m)

$^{19}$F NMR (CDCl$_3$):−58.4 (CF$_3$0,s); ca −127.5 (1F,dg)

GLC retention time:1.93 minutes

EXAMPLE 6

This Example illustrates the preparation of (RS)-1,1-difluoro-2-methyl-2-(4-trifluoromethoxyphenyl)propan-3-ol.

Methyl (RS)-1,1-difluoro-2-methyl-2-(4-trifluoromethoxyphenyl)propanoate (1.0g) was added dropwise to a stirred mixture of lithium aluminium hydride (0.12 g) and dry diethyl ether (20 cm$^3$); a vigorous reaction was observed. The mixture was stirred for a further 30 minutes, then poured into a mixture of ice, water and dilute aqueous hydrochloric acid solution. The aqueous mixture was extracted with chloroform, and the combined organic layers washed twice with water and dried over anhydrous magnesium sulphate. The solvent was evaporated under reduced pressure to leave a mobile liquid (0.95 g) which was purified by distillation under reduced pressure in a Kugelrohr apparatus. The title compound (0.82 g-98% pure by GLC) distilled in the range 160°-180° C. at a pressure of 20 mmHg.

$^1$H NMR (CDCl$_3$):1.48 (3H,s); 1.56 (1H,s); 3.94 (2H,s); 6.05 (1H,t,J=ca 56Hz); 7.2

7.5 (4H,m)

$^{19}$F NMR (CDCl$_3$):−58.4 (CF$_3$O); −128.5 (1F,dd)
GLC retention time:2.17 minutes.

EXAMPLE 7

This Example illustrates the preparation of 1,1-difluoro-2-(4-trifluoromethoxyphenyl)-3-(4-fluoro-3-phenoxybenzyloxy)propane.

1,1-Difluoro-2-methyl-2-(4-trifluoromethoxyphenyl)-propan-3-ol (0.8 g) was mixed with 3-phenoxy-4-fluorobenzyl bromide (0.83 g), sodium hydroxide (10 cm$^3$ of a 40% solution) dichloromethane (2cm$^3$) and tetra-n-butylammonium hydrogen sulphate (ca. 0.1 g). The reaction was stirred vigorously at room temperature for 4 hours, then was poured into water, acidified with dilute hydrochloric acid and extracted with chloroform. The combined chloroform extracts were washed with water, dried over anhydrous magnesium sulphate and the solvent evaporated under reduced pressure to give a viscous oil (1.45 g). The crude product was purified by column chromatography on silica gel, eluting with 5% ethyl acetate in hexane to give the title compound as an oil.

$^1$H NMR (CDCl$_3$):1.43 (3H, s); 3.6 (2H, ABg); 4.43 (2H, s); 6.00 (1H, t, J=56Hz); 7

7.5 (12H, m)

$^{19}$F NMR (CDCl$_3$):−58.3 (CF$_3$O, s); ca. −129.3 (CHF$_2$, dd, J=28, 56Hz); −132.7 (aromatic F, m).
GLC Retention Time:9.81 minutes

EXAMPLE 8

This Example illustrates the insecticidal and acaricidal properties of the Products of this invention.

The activity of the Product was determined using a variety of insect pests. The Product was used in the form of liquid preparations containing 500, 100 or 10 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

In the case of the species Musca domestica (housefly), additional tests to determine the knockdown effect of the compounds were performed. Details are given in Table I.

The results of the tests are given in Table II for each of the Products, at the rate in parts per million given in the second column as a grading of mortality designated as A, B or C wherein A indicates 80–100% mortality or knockdown, B indicates 50–79% mortality or knockdown and C indicates less than 50% mortality or knockdown.

In Table II the pest organism used is designated by a letter code and the pest species, the support medium or food, and the type and duration of test is given in Table I.

TABLE I

| CODE LETTERS (Table II) | TEST SPECIES | SUPPORT MEDIUM/FOOD | TYPE OF TEST | DURATION (days) |
| --- | --- | --- | --- | --- |
| TUa | Tetranychus urticae (spider mites - adult) | French bean leaf | Contact | 3 |
| TUe | Tetranychus urticae (spider mites - ova) | French bean leaf | Contact | 6 |
| MP | Myzus persicae (aphids) | Chinese Cabbage leaf | Contact | 3 |
| NC | Nephotettix cincticeps (green leaf hopper - nymphs) | Rice plant | Contact | 3 |
| HV | Heliothis virescens (tobacco budworm - larvae) | Cotton leaf | Residual | 3 |
| DB | Diabrotica balteata (rootworm larvae) | Filter paper/ maize seed) | Residual | 3 |
| BG | Blattella germanica (cockroach nymphs) | Plastic pot | Contact | 3 |
| MD | Musca domestica (houseflies - adults) | Cotton wool/ sugar | Contact | 1 |
| MD/KD | Musca domestica (houseflies - adults) | Cotton/wool sugar | Knockdown | 4 hours |
| SP | Spodoptera exiqua (lesser army worm - larvae) | Cotton leaf | Residual | 3 |

"Contact" test indicates that both pests and medium were treated and "residual" indicates that the medium was treated before infestation with the pests.

TABLE II

| PRODUCT | RATE (ppm) | TUa | TUe | MP | NC | NV | DB | BG | MD | MK/KD | SP |
| --- | --- | --- | --- | --- | --- | --- | --- | --- | --- | --- | --- |
| I | 100 | A | C | A | A | A | A | A | A | A | A |
| I | 10 | A | C | A | A | A | A | A | C | C | A |

EXAMPLE 9

This Example illustrates the acaricidal properties of the products of this invention.

French bean plants were grown to the two primary leaf stage and the growing tip was removed. The leaf area was reduced by trimming to form a "squared" area, and the trimmed leaves were infested with adult *Tetranychus urticae* mites by contact with a preinfested culture leaf. After 24 hours, leaf discs were cut from the infested plant and transferred to cooled agar bases contained in monopots. The pots were then sprayed with test chemical at the required rate in a Potter Tower. Following spraying, the mites were retained by covering the leaf disc with a netted plastic ring, and the discs held at 25° C. Assessment of mortality was carried out at 3 days after treatment. East test chemical was sprayed at five application rates and each treatment was replicated three times. A standard chemical was included in the test. The mortalities were statistically analysed to generate $LC_{50}$ concentrations (the calculated concentration of test chemical at which 50% mortality was achieved). Results were expressed for each test compound relative to the standard as an LC ratio defined as follows:

$$LC \text{ ratio} = \frac{LC_{50} \text{ of Test Chemical}}{LC_{50} \text{ of Standard Chemical}}$$

By this test procedure, it was established that Product I exhibits an LC ratio of 1.23 compared with the standard chemical, bifenthrin.

I claim:

1. A compound of formula:

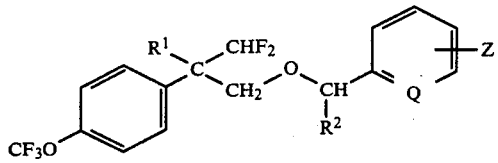

or a stereoisomer thereof, wherein $R^1$ represents alkyl containing up to four carbon atoms; $R^2$ is selected from hydrogen, cyano, methyl, trifluoromethyl and ethynyl; Q is carbon bearing a hydrogen atom; and Z represents one or more substituents selected from fluoro, benzyl, phenoxy, chlorophenoxy, fluorophenoxy and bromophenoxy.

2. A compound as claimed in claim 1, or a stereoisomer thereof, wherein $R^1$ represents methyl and wherein the group is selected from:
- 3-phenoxybenzyl
- 3-(4-chlorophenoxy)benzyl;
- 4-fluoro-3-(4-chlorophenoxy)benzyl;
- 3-benzyl-4-fluorobenzyl;
- and
- 1-cyano-1-(3-phenoxyphenyl)methyl.

3. 1,1-Difluoro-2-methyl-2-(4-trifluoromethoxyphenyl)-3-(4-fluoro-3-phenoxybenzyloxy)propane, or a stereoisomer thereof.

4. An insecticidal composition comprising an insecticidally effective amount of a compound according to claim 1 in association with an insecticidally inert diluent or carrier.

5. A method of combating insect pests at a locus which comprises treating the locus with an insecticidally effective amount of the composition of claim 4.

* * * * *